(12) United States Patent
Van Egmond et al.

(10) Patent No.: US 7,192,987 B2
(45) Date of Patent: Mar. 20, 2007

(54) PROCESSES FOR MAKING METHANOL STREAMS AND USES FOR THE STREAMS

(75) Inventors: Cor F. Van Egmond, Pasadena, TX (US); Teng Xu, Houston, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 502 days.

(21) Appl. No.: 10/793,713

(22) Filed: Mar. 5, 2004

(65) Prior Publication Data

US 2005/0197412 A1    Sep. 8, 2005

(51) Int. Cl.
*C07C 27/00* (2006.01)
*C07C 1/00* (2006.01)

(52) U.S. Cl. ............ 518/700; 585/638; 585/639; 585/640

(58) Field of Classification Search ......... 518/700; 585/638–640
See application file for complete search history.

(56) References Cited

U.S. PATENT DOCUMENTS

| | | | |
|---|---|---|---|
| 4,455,394 A | 6/1984 | Pinto | 518/704 |
| 4,592,806 A | 6/1986 | Ilgner et al. | 203/71 |
| 4,605,677 A | 8/1986 | Knifton | 518/700 |
| 4,927,857 A | 5/1990 | McShea, III et al. | 518/703 |
| 5,063,250 A | 11/1991 | Murayama et al. | 518/704 |
| 5,346,593 A | 9/1994 | Cialkowski et al. | 203/18 |
| 5,387,322 A | 2/1995 | Cialkowski et al. | 252/158 |
| 5,714,662 A | 2/1998 | Vora et al. | 585/640 |
| 6,258,860 B1 | 7/2001 | Weedon et al. | 518/706 |
| 6,441,262 B1 | 8/2002 | Fung et al. | 585/640 |
| 6,444,712 B1 | 9/2002 | Janda | 518/706 |
| 6,486,219 B1 | 11/2002 | Janda et al. | 518/706 |
| 2004/0034265 A1 | 2/2004 | Janssen et al. | 585/640 |

FOREIGN PATENT DOCUMENTS

| | | |
|---|---|---|
| DE | 257 740 | 6/1988 |
| GB | 2 078 745 | 1/1982 |

OTHER PUBLICATIONS

Thomson Derwent Abstract for DD 257740, Jun. 29, 1988 entitled "Catalysts and Process for C2-4 Olefin Manufacture from Methanol-Containing Alcohol Mixtures".

*Primary Examiner*—J. Parsa

(57) ABSTRACT

This invention is directed to processes (i.e., methods) for making methanol compositions, and to processes (i.e., methods) of using the methanol compositions. The methanol compositions contain ethanol and are particularly suitable for contacting with an olefin forming catalyst to form an olefin stream.

64 Claims, No Drawings

PROCESSES FOR MAKING METHANOL STREAMS AND USES FOR THE STREAMS

FIELD OF THE INVENTION

This invention is to processes for making methanol streams and processes for using the streams. In particular, this invention concerns processes for making methanol streams that contain higher than conventional quantities of ethanol, and processes for using the methanol streams.

BACKGROUND OF THE INVENTION

Methanol is a major chemical raw material used to make a variety of products, including acetic acid, formaldehyde, and methyl tertiary butyl ether. Worldwide demand is expected to significantly increase as new applications for the use of methanol become commercialized. Such new applications include the conversion of methanol to gas, such as the Mobil MTG process; the conversion of methanol to olefins, gasoline and distillate, such as the Mobil MOGD process; and the conversion of methanol to olefins, such as the MTO process.

For example, in U.S. Pat. Nos. 6,444,712 B1 and 6,486,219 B1 to Janda, a method for producing olefins from methanol, by way of using natural gas to make the methanol, is described. The method includes converting the methane component of the natural gas to synthesis gas (syngas) using a steam reformer and a partial oxidation reformer. The syngas from each reformer is combined and sent to a methanol synthesis reactor. The combined syngas stream to the methanol synthesis reactor desirably has a syngas number of from about 1.4 to 2.6. The methanol product is then used as a feed in a methanol to olefin production process.

Much of the methanol made today is made under high purity specifications. Grade A and grade AA methanol are commonly produced. U.S. Pat. No. 4,592,806 to Ilgner discloses a process for producing the grade AA methanol. The grade AA methanol has a maximum ethanol content of 10 ppm and is produced using a distillation column, and distilling fusel oil at a reflux ratio of at least 5:1.

The use of crude, or substantially unrefined, methanol has been suggested for use in making olefins. In U.S. Pat. No. 5,714,662 to Vora, there is disclosed an integrated process for producing light olefins from a hydrocarbon gas stream by combining reforming, methanol production, and methanol conversion. The methanol produced is a crude methanol, which is essentially unrefined and comprises methanol, light ends, and heavier alcohols. The crude methanol is passed directly to an oxygenate conversion zone to produce light olefins.

As the production of methanol continues to increase, and the new commercial uses of methanol also continue to increase, it would be advantageous to produce variable quality methanol streams, which have particular advantages for specific end uses, and which do not have to meet the stringent requirements of Grades AA and A methanol. It would also be beneficial to provide various processes for which the methanol streams would be of particular benefit.

SUMMARY OF THE INVENTION

This invention provides for processes of making methanol compositions that contain variable quantities of ethanol. In addition, the invention provides various methods for which the methanol compositions would be of particular benefit.

In one aspect, this invention provides a process for making a methanol product stream. In one embodiment, the process comprises contacting a synthesis gas with a carbon oxide conversion catalyst to form a crude methanol stream. The crude methanol stream is distilled in a distillation system to form a methanol product stream, a water containing stream, and, optionally, a fusel oil containing stream.

In one embodiment the methanol product stream is recovered from the distillation system at a weight ratio of the fusel oil containing stream to the methanol product stream of not greater than 0.5 to 1. Preferably, the methanol product stream is recovered at a weight ratio of the fusel oil stream to the methanol product stream of not greater than 0.3 to 1, more preferably not greater than 0.2 to 1, still more preferably not greater than 0.1 to 1, and most preferably not greater than 0.05 to 1. In particular, the methanol product stream can be recovered at a ration ratio of the fusel oil stream to the methanol product stream of down to 0.

The processes of this invention provide for the manufacture of methanol in large-scale quantities (e.g., quantities of at least 10,000 gallons) for conversion to a variety of derivative products. An example of one derivate product includes olefins, which is of great advantage for further conversion of the olefins to polyolefins such as polyethylene and polypropylene. In one embodiment, the methanol composition is produced and transported to a location geographically distinct from that where it was manufactured. Preferably, the methanol composition s loaded onto a vessel, and the vessel is transported over a body of water to a storage facility or directly to a conversion unit.

In other embodiments, the methanol product composition that is recovered, preferably from distillation, comprises at least 75 wt %, 80 wt %, 85 wt %, or 90 wt % methanol, based on total weight of the methanol composition. In yet other embodiments the methanol composition comprises not greater than 99 wt %, 98 wt %, 97 wt %, or 96 wt % methanol, based on total weight of the methanol composition.

The recovered methanol product composition preferably comprises at least 10 wppm, 100 wppm, 1,000 wppm, 10,000 wppm, or 0.1 wt % ethanol, based on total weight of the methanol composition. Alternatively, the recovered methanol product composition comprises not greater than 50 wt %, 40 wt %, 35 wt %, or not greater than 30 wt % ethanol, based on total weight of the methanol composition.

In one embodiment, the recovered methanol product composition further comprises at least 0.1 wt % water, 0.15 wt %, 0.2 wt %, or 0.25 wt % water, based on total weight of the methanol composition. Preferably, the methanol composition further comprises not greater than 2 wt %, 1.5 wt %, or 1.2 wt % water, based on total weight of the methanol composition.

There is further provided a process for making an olefin stream from the methanol stream. In one embodiment, the process comprises contacting a synthesis gas stream with a carbon oxide conversion catalyst to form a crude methanol stream containing methanol and ethanol. A methanol composition rich in ethanol is separated from the crude methanol stream, wherein the methanol composition comprises a majority of the methanol and a majority of the ethanol contained in the crude methanol stream. The separated methanol composition is then contacted with an olefin forming catalyst to form an olefin stream.

A variety of hydrocarbons can be used to form the crude methanol stream. Examples of such hydrocarbons include biomass, natural gas, $C_1$ to $C_5$ hydrocarbons, naphtha, heavy petroleum coils, coke, and mixtures thereof. A methane containing gas is a preferred hydrocarbon to use in making the crude methanol stream.

In one embodiment, hydrocarbon is converted to synthesis gas, then the synthesis gas is converted to crude methanol. The methanol composition containing the ethanol is then separated from the crude methanol.

In another embodiment of the invention, a synthesis gas stream is contacted with a carbon oxide conversion catalyst to form a crude methanol stream. The crude methanol stream is preferably distilled and a methanol stream containing ethanol is recovered.

In one embodiment of the invention, the methanol product stream that is recovered is contacted with an olefin forming catalyst to form an olefin stream. Preferably, at least a portion of the olefins in the olefin stream are contacted with a polymerization catalyst to form a polyolefin. Preferred polyolefins are polyethylene and polypropylene.

DETAILED DESCRIPTION OF THE INVENTION

I. Introduction

This invention is directed to processes (i.e., methods) for making methanol product compositions, and to processes (i.e., methods) of using the methanol product compositions. The methanol product compositions are refined from crude methanol compositions, and are particularly suitable for contacting with an olefin forming catalyst to form an olefin stream, and can be made from various carbon materials at a relatively large scale for commercial scale processing and upgrading. The processes of this invention allow for transporting the manufactured or refined methanol compositions to geographically distinct locations fairly remote from the site of manufacture for use as a feed stock to a variety of processes.

The processes by which the methanol product compositions or streams are made according to this invention result in an increased quantity of ethanol in the methanol stream relative to conventional methanol streams such as Grade AA and A methanol streams. The methanol product streams are particularly suitable for use as a feed stream in a catalytic process, particularly processes that use an olefin forming catalyst to convert the methanol and ethanol to ethylene and propylene, particularly ethylene. The ethylene and propylene are then recovered and used for further processing, such as in the manufacture of polyethylene and polypropylene.

The processes for manufacturing the methanol product streams of this invention involve distilling a crude methanol stream to form a methanol product stream, a water containing stream, and an optional fusel oil containing stream. It is preferred that the amount of fusel oil recovered as a separate stream or draw stream be limited so as to increase the concentration of ethanol in the methanol stream. It is also preferred that the amount of fusel oil recovered as a separate stream be limited so as to limit the methanol concentration in the water containing stream. As a result, the recovered methanol stream is particularly beneficial for use in a methanol to olefins conversion process, as the recovered methanol stream will increase ethylene production in such a process. The water containing stream that is recovered according to the process of the invention can be sent directly to a waste treatment system, if desired, without a significant added biological load to the system.

II. Method of Making Crude Methanol Compositions

A. Examples of Methanol Synthesis Processes

The methanol product composition of this invention can be derived from a variety of hydrocarbon sources. Examples of such sources include biomass, natural gas, $C_1$–$C_5$ hydrocarbons, naphtha, heavy petroleum oils, or coke (i.e., coal). Preferably, the hydrocarbon sources comprise methane in an amount of at least about 50% by volume, more preferably at least about 70% by volume, most preferably at least about 80% by volume. In one embodiment of this invention, natural gas is the preferred hydrocarbon source.

One way of converting the carbon source to a methanol composition is to first convert the carbon source to synthesis gas (syngas), and then convert the syngas to a crude methanol composition. The crude methanol composition is then processed to form the methanol product composition. Any conventional process can be used. In particular, any conventional carbon oxide conversion catalyst can be used to convert the syngas to the crude methanol composition. In one embodiment, the carbon oxide conversion catalyst is a nickel containing catalyst.

Synthesis gas comprises carbon monoxide and hydrogen. Optionally, carbon dioxide and nitrogen are included. Conventional processes for converting carbon components to syngas include steam reforming, partial oxidation, and autothermal reforming.

The hydrocarbon feed stream that is used in the conversion of hydrocarbon to synthesis gas, is optionally treated to remove impurities that can cause problems in further processing of the hydrocarbon feed stream. These impurities can poison many conventional propylene and ethylene forming catalysts. A majority of the impurities, which may be present, can be removed in any conventional manner. The hydrocarbon feed is preferably purified to remove sulfur compounds, nitrogen compounds, particulate matter, other condensables, and/or other potential catalyst poisons prior to being converted into synthesis gas.

In one embodiment of the invention, the hydrocarbon feed stream is passed to a synthesis gas plant. Synthesis gas refers to a combination of hydrogen and carbon oxide produced in a synthesis gas plant from a hydrocarbon feed, the synthesis gas having an appropriate molar ratio of hydrogen to carbon oxide (carbon monoxide and/or carbon dioxide), as described below. The synthesis gas plant may employ any conventional means of producing synthesis gas, including partial oxidation, steam or $CO_2$ reforming, or some combination of these two chemistries.

Steam reforming generally comprises contacting a hydrocarbon with steam to form synthesis gas. The process preferably includes the use of a catalyst.

Partial oxidation generally comprises contacting a hydrocarbon with oxygen or an oxygen containing gas such as air to form synthesis gas. Partial oxidation takes place with or without the use of a catalyst, although the use of a catalyst is preferred. In one embodiment, water (steam) is added with the feed in the partial oxidation process. Such an embodiment is generally referred to as autothermal reforming.

Conventional synthesis gas-generating processes include gas phase partial oxidation, autothermal reforming, fluid bed synthesis gas generation, catalytic partial oxidation and various processes for steam reforming.

B. Steam Reforming to Make Syngas

In the catalytic steam reforming process, hydrocarbon feeds are converted to a mixture of $H_2$, $CO$ and $CO_2$ by reacting hydrocarbons with steam over a catalyst. This process involves the following reactions:

$$CH_4 + H_2O \rightleftharpoons CO + 3H \quad (1)$$

or $$C_nH_m + nH_2O \rightleftharpoons nCO + [n+(m/2)]H_2 \quad (2)$$

and $$CO + H_2O \rightleftharpoons CO_2 + H_2 \quad (3) \text{ (shift reaction)}$$

The reaction is carried out in the presence of a catalyst. Any conventional reforming type catalyst can be used. The catalyst used in the step of catalytic steam reforming comprises at least one active metal or metal oxide of Group 6 or Group 8–10 of the Periodic Table of the Elements. The Periodic Table of the Elements referred to herein is that from *CRC Handbook of Chemistry and Physics*, 82$^{nd}$ Edition, 2001–2002, CRC Press LLC, which is incorporated herein by reference.

In one embodiment, the catalyst contains at least one Group 6 or Group 8–10 metal, or oxide thereof, having an atomic number of 28 or greater. Specific examples of reforming catalysts that can be used are nickel, nickel oxide, cobalt oxide, chromia and molybdenum oxide. Optionally, the catalyst is employed with least one promoter. Examples of promoters include alkali and rare earth promoters. Generally, promoted nickel oxide catalysts are preferred.

The amount of Group 6 or Group 8–10 metals in the catalyst can vary. Preferably, the catalyst includes from about 3 wt % to about 40 wt % of at least one Group 6 or Group 8–10 metal, based on total weight of the catalyst. Preferably, the catalyst includes from about 5 wt % to about 25 wt % of at least one Group 6 or Group 8–10 metal, based on total weight of the catalyst.

The reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are preferably included in the catalyst in an amount of from about 0.1 wt % to about 30 wt %, based on total weight of nickel in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons higher than methane. The concentration of such platinum group metal is typically in the range 0.0005 to 0.1% as metal, calculated as the whole catalyst unit. Further, the catalyst, especially in preferred forms, can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is in the range 0.0005 to 0.5% w/w as metal, calculated on the whole catalytic unit.

In one embodiment, the reformer unit includes tubes which are packed with solid catalyst granules. Preferably, the solid catalyst granules comprise nickel or other catalytic agents deposited on a suitable inert carrier material. More preferably, the catalyst is NiO supported on calcium aluminate, alumina, spinel type magnesium aluminum oxide or calcium aluminate titanate.

In yet another embodiment, both the hydrocarbon feed stream and the steam are preheated prior to entering the reformer. The hydrocarbon stream is preheated up to as high a temperature as is consistent with the avoiding of undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C.; preferably at least 400° C. The reforming reaction is generally carried out at a reformer temperature of from about 500° C. to about 1,200° C., preferably from about 800° C. to about 1,100° C., and more preferably from about 900° C. to about 1,050° C.

Gas hourly space velocity in the reformer should be sufficient for providing the desired CO to $CO_2$ balance in the synthesis gas. Preferably, the gas hourly space velocity (based on wet feed) is from about 3,000 per hour to about 10,000 per hour, more preferably from about 4,000 per hour to about 9,000 per hour, and most preferably from about 5,000 per hour to about 8,000 per hour.

Any conventional reformer can be used in the step of catalytic steam reforming. The use of a tubular reformer is preferred. Preferably, the hydrocarbon feed is passed to a tubular reformer together with steam, and the hydrocarbon and steam contact a steam reforming catalyst. In one embodiment, the steam reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, *Encyclopedia of Chemical Technology*, 3rd Ed., 1990, vol. 12, p. 951; and *Ullmann's Encyclopedia of Industrial Chemistry*, 5th Ed., 1989, vol. A-12, p. 186, the relevant portions of each being fully incorporated herein by reference.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. On this basis, the mole ratio of steam to hydrocarbon feed in the conventional primary reformer unit is preferably from about 1.5:1 to about 5:1, preferably from about 2:1 to about 4:1.

The hydrogen to carbon oxide ratio of the synthesis gas produced will vary depending on the overall conditions of the reformer. Preferably, the molar ratio of hydrogen to carbon oxide in the synthesis gas will range from about 1:1 to about 5:1. More preferably the molar ratio of hydrogen to carbon oxide will range from about 2:1 to about 3:1. Even more preferably the molar ratio of hydrogen to carbon oxide will range from about 2:1 to about 2.5:1. Most preferably the molar ration of hydrogen to carbon oxide will range from about 2:1 to about 2.3:1.

Steam reforming is generally carried out at superatmospheric pressure. The specific operating pressure employed is influenced by the pressure requirements of the subsequent process in which the reformed gas mixture is to be employed. Although any superatmospheric pressure can be used in practicing the invention, pressures of from about 175 psig (1,308 kPa abs.) to about 1,100 psig (7,686 kPa abs.) are desirable. Preferably, steam reforming is carried out at a pressure of from about 300 psig (2,170 kPa abs.) to about 800 psig (5,687 kPa abs.), more preferably from about 350 psig (2,515 kPa abs.) to about 700 psig (4,928 kPa abs.).

C. Partial Oxidation to Make Syngas

The invention further provides for the production of synthesis gas, or CO and $H_2$, by oxidative conversion (also referred to herein as partial oxidation) of hydrocarbon, particularly natural gas and $C_1$–$C_5$ hydrocarbons. According to the process, hydrocarbon is reacted with free-oxygen to form the CO and $H_2$. The process is carried out with or without a catalyst. The use of a catalyst is preferred, preferably with the catalyst containing at least one non-transition or transition metal oxides. The process is essentially exothermic, and is an incomplete combustion reaction, having the following general formula:

$$C_nH_m + (n/2)O_2 \rightleftharpoons nCO + (m/2)H_2 \quad (4)$$

Non-catalytic partial oxidation of hydrocarbons to $H_2$, CO and $CO_2$ is desirably used for producing syngas from heavy fuel oils, primarily in locations where natural gas or lighter hydrocarbons, including naphtha, are unavailable or uneconomical compared to the use of fuel oil or crude oil. The non-catalytic partial oxidation process is carried out by injecting preheated hydrocarbon, oxygen and steam through a burner into a closed combustion chamber. Preferably, the individual components are introduced at a burner where they meet in a diffusion flame, producing oxidation products and heat. In the combustion chamber, partial oxidation of the hydrocarbons generally occurs with less than stoichiometric oxygen at very high temperatures and pressures. Preferably, the components are preheated and pressurized to reduce reaction time. The process preferably occurs at a temperature of from about 1,350° C. to about 1,600° C., and at a pressure of from above atmospheric to about 150 atm.

Catalytic partial oxidation comprises passing a gaseous hydrocarbon mixture, and oxygen, preferably in the form of air, over reduced or unreduced composite catalysts. The reaction is optionally accompanied by the addition of water vapor (steam). When steam is added, the reaction is generally referred to as autothermal reduction. Autothermal reduction is both exothermic and endothermic as a result of adding both oxygen and water.

In the partial oxidation process, the catalyst comprises at least one transition element selected from the group consisting of Ni, Co, Pd, Ru, Rh, Ir, Pt, Os and Fe. Preferably, the catalyst comprises at least one transition element selected from the group consisting of Pd, Pt, and Rh. In another embodiment, preferably the catalyst comprises at least one transition element selected form the group consisting of Ru, Rh, and Ir.

In one embodiment, the partial oxidation catalyst further comprises at least one metal selected from the group consisting of Ti, Zr, Hf, Y, Th, U, Zn, Cd, B, Al, Tl, Si, Sn, Pb, P, Sb, Bi, Mg, Ca, Sr, Ba, Ga, V, and Sc. Also, optionally included in the partial oxidation catalyst is at least one rare earth element selected from the group consisting of La, Ce, Pr, Nd, Pm, Sm, Eu, Gd, Th, Dy, Ho, Er, Tm, Yb and Lu.

In another embodiment the catalyst employed in the process may comprise a wide range of catalytically active components, for example Pd, Pt, Rh, Ir, Os, Ru, Ni, Cr, Co, Ce, La and mixtures thereof. Materials not normally considered to be catalytically active may also be employed as catalysts, for example refractory oxides such as cordierite, mullite, mullite aluminium titanate, zirconia spinels and alumina.

In yet another embodiment, the catalyst is comprised of metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the partial oxidation catalyst comprises at least one transition or non-transition metal deposited on a monolith support. The monolith supports are preferably impregnated with a noble metal such as Pt, Pd or Rh, or other transition metals such as Ni, Co, Cr and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

In one embodiment, the catalyst is retained in form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

In yet another embodiment, the feed comprises methane, and the feed is injected with oxygen into the partial oxidation reformer at a methane to oxygen (i.e., $O_2$) ratio of from about 1.2:1 to about 10:1. Preferably the feed and oxygen are injected into the reformer at a methane to oxygen ratio of from about 1.6:1 to about 8:1, more preferably from about 1.8:1 to about 4:1.

Water may or may not be added to the partial oxidation process. When added, the concentration of water injected into the reformer is not generally greater than about 65 mole %, based on total hydrocarbon and water feed content. Preferably, when water is added, it is added at a water to methane ratio of not greater than 3:1, preferably not greater than 2:1.

The catalyst may or may not be reduced before the catalytic reaction. In one embodiment, the catalyst is reduced and reduction is carried out by passing a gaseous mixture comprising hydrogen and inert gas (e.g., $N_2$, He, or Ar) over the catalyst in a fixed bed reactor at a catalyst reduction pressure of from about 1 atm to about 5 atm, and a catalyst reduction temperature of from about 300° C. to about 700° C. Hydrogen gas is used as a reduction gas, preferably at a concentration of from about 1 mole % to about 100 mole %, based on total amount of reduction gas. Desirably, the reduction is further carried out at a space velocity of reducing gas mixture of from about $10^3$ cm$^3$/g·hr to about $10^5$ cm$^3$/g·hr for a period of from about 0.5 hour to about 20 hours.

In one embodiment, the partial oxidation catalyst is not reduced by hydrogen. When the catalyst is not reduced by hydrogen before the catalytic reaction, the reduction of the catalyst can be effected bypassing the hydrocarbon feed and oxygen (or air) over the catalyst at temperature in the range of from about 500° C. to about 900° C. for a period of from about 0.1 hour to about 10 hours.

In the partial oxidation process, carbon monoxide (CO) and hydrogen ($H_2$) are formed as major products, and water and carbon dioxide ($CO_2$) as minor products. The gaseous product stream comprises the above mentioned products, unconverted reactants (i.e. methane or natural gas and oxygen) and components of feed other than reactants.

When water is added in the feed, the $H_2$:CO mole ratio in the product is increased by the shift reaction:

$CO + H_2O \leftrightarrows H_2 + CO_2$. This reaction occurs simultaneously with the oxidative conversion of the hydrocarbon in the feed to CO and $H_2$ or synthesis gas. The hydrocarbon used as feed in the partial oxidation process is preferably in the gaseous phase when contacting the catalyst. The partial oxidation process is particularly suitable for the partial oxidation of methane, natural gas, associated gas or other sources of light hydrocarbons. In this respect, the term "light hydrocarbons" is a reference to hydrocarbons having from 1 to 5 carbon atoms. The process may be advantageously applied in the conversion of gas from naturally occurring reserves of methane which contain substantial amounts of carbon dioxide. In one embodiment, the hydrocarbon feed preferably contains from about 10 mole % to about 90 mole % methane, based on total feed content. More preferably, the hydrocarbon feed contains from about 20 mole % to about 80 mole % methane, based on total feed content. In another embodiment, the feed comprises methane in an amount of at least 50% by volume, more preferably at least 70% by volume, and most preferably at least 80% by volume.

In one embodiment of the invention, the hydrocarbon feedstock is contacted with the catalyst in a mixture with an oxygen-containing gas. Air is suitable for use as the oxygen-containing gas. Substantially pure oxygen as the oxygen-containing gas is preferred on occasions where there is a need to avoid handling large amounts of inert gas such as nitrogen. The feed optionally comprises steam.

In another embodiment of the invention, the hydrocarbon feedstock and the oxygen-containing gas are preferably present in the feed in such amounts as to give an oxygen-to-carbon ratio in the range of from about 0.3:1 to about 0.8:1, more preferably, in the range of from about 0.45:1 to about 0.75:1. References herein to the oxygen-to-carbon ratio refer to the ratio of oxygen in the from of oxygen molecules ($O_2$) to carbon atoms present in the hydrocarbon feedstock. Preferably, the oxygen-to-carbon ratio is in the range of from about 0.45:1 to about 0.65:1, with oxygen-to-carbon ratios in the region of the stoichiometric ratio of 0.5:1, that is ratios in the range of from about 0.45:1 to about 0.65:1, being more preferred. When steam is present in the feed, the steam-to-carbon ratio is not greater than about 3.0:1, more preferably not greater than about 2.0:1. The hydrocarbon feedstock, the oxygen-containing gas and steam, if present, are preferably well mixed prior to being contacted with the catalyst.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 bars. Preferably, the partial oxidation process is operated at a pressure in the range of from about 2 bars to about 125 bars, more preferably from about 5 bars to about 100 bars.

The partial oxidation process is also operable over a wide range of temperatures. At commercial scale, the feed is preferably contacted with the catalyst at high temperatures. In one embodiment, the feed mixture is contacted with the catalyst at a temperature in excess of 600° C. Preferably, the feed mixture is contacted with the catalyst at a temperature in the range of from about 600° C. to about 1,700° C., more preferably from about 800° C. to about 1,600° C. The feed mixture is preferably preheated prior to contacting the catalyst.

The feed is provided during the operation of the process at a suitable space velocity to form a substantial amount of CO in the product. In one embodiment, gas space velocities (expressed in normal liters of gas per kilogram of catalyst per hour) are in the range of from about 20,000 Nl/kg/hr to about 100,000,000 Nl/kg/hr, more preferably in the range of from about 50,000 Nl/kg/hr to about 50,000,000 Nl/kg/hr, and most preferably in the range of from about 500,000 Nl/kg/hr to about 30,000,000 Nl/kg/hr.

D. Combination Syngas Processes

Combination reforming processes can also be incorporated into this invention. Examples of combination reforming processes include autothermal reforming and fixed bed syngas generation. These processes involve a combination of gas phase partial oxidation and steam reforming chemistry.

The autothermal reforming process preferably comprises two synthesis gas generating processes, a primary oxidation process and a secondary steam reforming process. In one embodiment, a hydrocarbon feed stream is steam reformed in a tubular primary reformer by contacting the hydrocarbon and steam with a reforming catalyst to form a hydrogen and carbon monoxide containing primary reformed gas, the carbon monoxide content of which is further increased in the secondary reformer. In one embodiment, the secondary reformer includes a cylindrical refractory lined vessel with a gas mixer, preferably in the form of a burner in the inlet portion of the vessel and a bed of nickel catalyst in the lower portion. In a more preferred embodiment, the exit gas from the primary reformer is mixed with air and residual hydrocarbons, and the mixed gas partial oxidized to carbon monoxides.

In another embodiment incorporating the autothermal reforming process, partial oxidation is carried out as the primary oxidating process. Preferably, hydrocarbon feed, oxygen, and optionally steam, are heated and mixed at an outlet of a single large coaxial burner or injector which discharges into a gas phase partial oxidation zone. Oxygen is preferably supplied in an amount which is less than the amount required for complete combustion.

Upon reaction in the partial oxidation combustion zone, the gases flow from the primary reforming process into the secondary reforming process. In one embodiment, the gases are passed over a bed of steam reforming catalyst particles or a monolithic body, to complete steam reforming. Desirably, the entire hydrocarbon conversion is completed by a single reactor aided by internal combustion.

In an alternative embodiment of the invention, a fixed bed syngas generation process is used to form synthesis gas. In the fixed bed syngas generation process, hydrocarbon feed and oxygen or an oxygen-containing gas are introduced separately into a fluid catalyst bed. Preferably, the catalyst is comprised of nickel and supported primarily on alpha alumina.

The fixed bed syngas generation process is carried out at conditions of elevated temperatures and pressures that favor the formation of hydrogen and carbon monoxide when, for example, methane is reacted with oxygen and steam. Preferably, temperatures are in excess of about 1,700° F. (927° C.), but not so high as to cause disintegration of the catalyst or the sticking of catalyst particles together. Preferably, temperatures range from about 1,750° F. (954° C.) to about 1,950° F. (1,066° C.), more preferably, from about 1,800° F. (982° C.) to about 1,850° F. (1,010° C.).

Pressure in the fixed bed syngas generation process may range from atmospheric to about 40 atmospheres. In one embodiment, pressures of from about 20 atmospheres to about 30 atmospheres are preferred, which allows subsequent processes to proceed without intermediate compression of product gases.

In one embodiment of the invention, methane, steam, and oxygen are introduced into a fluid bed by separately injecting the methane and oxygen into the bed. Alternatively, each stream is diluted with steam as it enters the bed. Preferably, methane and steam are mixed at a methane to steam molar ratio of from about 1:1 to about 3:1, and more preferably from about 1.5:1 to about 2.5:1, and the methane and steam mixture is injected into the bed. Preferably, the molar ratio of oxygen to methane is from about 0.2:1 to about 1.0:1, more preferably from about 0.4:1 to about 0.6:1.

In another embodiment of the invention, the fluid bed process is used with a nickel based catalyst supported on alpha alumina. In another embodiment, silica is included in the support. The support is preferably comprised of at least 95 wt % alpha alumina, more preferably at least about 98% alpha alumina, based on total weight of the support.

In one embodiment, a gaseous mixture of hydrocarbon feedstock and oxygen-containing gas are contacted with a reforming catalyst under adiabatic conditions. For the purposes of this invention, the term "adiabatic" refers to reaction conditions in which substantially all heat loss and radiation from the reaction zone are prevented, with the exception of heat leaving in the gaseous effluent stream of the reactor.

E. Converting Syngas to Crude Methanol

The synthesis gas is sent to a methanol synthesis process and converted to a crude methanol stream. In one embodiment, the crude methanol stream is distilled to remove a portion of the undesirable components in the crude methanol stream. Preferably, the methanol synthesis process is accomplished in the presence of a methanol synthesis catalyst and produces a significant quantity of ethanol. The crude methanol stream is distilled so as to recover the ethanol along with the final methanol product.

In one embodiment, the synthesis gas is sent as is to the methanol synthesis process. In another embodiment, the hydrogen, carbon monoxide, and/or carbon dioxide content of the synthesis gas is adjusted for efficiency of conversion. Desirably, the synthesis gas input to the methanol synthesis reactor has a molar ratio of hydrogen ($H_2$) to carbon oxides ($CO+CO_2$) in the range of from about 0.5:1 to about 20:1, preferably in the range of from about 2:1 to about 10:1. In another embodiment, the synthesis gas has a molar ratio of hydrogen ($H_2$) to carbon monoxide (CO) of at least 4:1. Carbon dioxide is optionally present in an amount of not greater than 50% by weight, based on total weight of the synthesis gas.

Desirably, the stoichiometric molar ratio is sufficiently high so as maintain the conversion of CO and $H_2$ to methanol, but not so high in $H_2$ as to reduce the volume productivity of methanol. Preferably, the synthesis gas fed to the methanol synthesis has a stoichiometric molar ratio (i.e., a molar ratio of $H_2:(2CO+3CO_2)$) of from about 1.0:1 to about 2.7:1, more preferably from about 1.1 to about 2.0, more preferably a stoichiometric molar ratio of from about 1.2:1 to about 1.8:1.

The $H_2$ content, relative to that of CO, in the synthesis gas should be high enough so as to maintain an appropriately high reaction temperature and to minimize the amount of undesirable by-products such as paraffins. At the same time, the relative $CO_2$ to CO content should not be too high so as to reduce methanol yield. Desirably, the synthesis gas contains $CO_2$ and CO at a ratio of from about 0.3 to about 1.2, preferably from about 0.4 to about 1.0.

In addition, the $CO_2$ content and catalyst type are preferably selected so as to achieve a suitable ethanol to water ratio in the crude methanol composition. If the ethanol content of the crude methanol composition is too high relative to the water content, the final distilled methanol product stream will generally contain too much water. If the ethanol content of the crude methanol composition is too low, the final distilled methanol product stream will generally contain too little ethanol in the final distilled methanol product stream to be of significant benefit in an oxygenate to olefin conversion reaction.

In one embodiment, the crude methanol composition includes ethanol and water at an ethanol to water ratio of not greater than 1.5:1. Preferably, the crude methanol composition includes ethanol and water at an ethanol to water ratio of not greater than 1.3:1, more preferably not greater than 1.2:1, and most preferably not greater than 1:1. It is also preferred that the crude methanol composition includes at least 1 wt % ethanol, based on total weight of the composition. Preferably, the crude methanol composition includes at least 5 wt % ethanol, more preferably at least 10 wt % ethanol, and most preferably at least 15 wt % ethanol based on total weight of the composition.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium and zirconium. Preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

The methanol synthesis catalyst is made according to conventional processes. Examples of such processes can be found in U.S. Pat. Nos. 6,114,279; 6,054,497; 5,767,039; 5,045,520; 5,254,520; 5,610,202; 4,666,945; 4,455,394; 4,565,803; 5,385,949, with the descriptions of each being fully incorporated herein by reference.

In one embodiment, the synthesis gas formed in the synthesis gas conversion plant is cooled prior to sending to the methanol synthesis reactor. Preferably, the synthesis gas is cooled so as to condense at least a portion of the water vapor formed during the synthesis gas process.

The methanol synthesis process used to manufacture the methanol composition of this invention can be any conventional process. Examples of such processes include batch processes and continuous processes. Continuous processes are preferred. Tubular bed processes and fluidized bed processes are particularly preferred types of continuous processes.

In general, the methanol synthesis process takes place according to the following reactions:

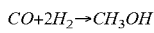

$CO+2H_2 \rightarrow CH_3OH$

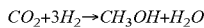

$CO_2+3H_2 \rightarrow CH_3OH+H_2O$

The methanol synthesis process is effective over a wide range of temperatures. In one embodiment, the synthesis gas is contacted with the methanol synthesis catalyst at a temperature in the range of from about 150° C. to about 450° C., preferably in a range of from about 175° C. to about 350° C., more preferably in a range of from about 200° C. to about 300° C.

The process is also operable over a wide range of pressures. In one embodiment, the synthesis gas is contacted with the methanol synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres.

Gas hourly space velocities vary depending upon the type of continuous process that is used. Desirably, gas hourly space velocity of flow of gas through the catalyst bed is in the range of from about 50 hr$^{-1}$ to about 50,000 hr$^{-1}$. Preferably, gas hourly space velocity of flow of gas through the catalyst bed is in the range of from about 250 hr$^{-1}$ to about 25,000 hr$^{-1}$, more preferably from about 500 hr$^{-1}$ to about 10,000 hr$^{-1}$.

F. Refining Crude Methanol to Make Methanol Product

A crude methanol stream produced according to this invention is further processed to obtain the methanol product composition of the invention that contains higher than typical levels of ethanol. In one embodiment of the invention, the crude methanol stream is sent from a methanol synthesizing unit to a distillation system. The distillation system contains one or more distillation columns that are used to separate the desired methanol composition from a separate water stream, and an optional fusel oil stream. Desirably, the methanol composition that is separated and recovered from the crude methanol stream comprises a majority of the methanol and a majority of the ethanol contained in the crude methanol stream.

In another embodiment, the distillation system includes a step of treating the methanol steam being distilled so as to remove or neutralize acids in the recovered stream. Preferably, the methanol stream is treated by adding a base that is effective in neutralizing organic acids found in the methanol stream. Conventional base compounds can be used. Examples of base compounds include alkali metal hydroxide or carbonate compounds, and amine or ammonium hydroxide compounds. In one particular embodiment, about 20 ppm to about 120 ppm w/w of a base composition, calculated as stoichiometrically equivalent NaOH, is added, preferably about 25 ppm to about 100 ppm w/w of a base composition, calculated as stoichiometrically equivalent NaOH, is added.

The invention can include any distillation system that produces a methanol product stream, a water stream, as well as an optional "fusel oil" stream (i.e., a stream having a majority of hydrocarbon compounds with a boiling point greater than that of methanol). Preferably, the methanol product stream, which contains ethanol, is recovered as an overhead or upper stream, and the water stream is recovered as a bottoms draw or lower stream from the distillation system.

It is preferred that the methanol product composition that is recovered from the distillation system contain less than 99.85 wt % methanol, based on total weight of the composition, and contain an amount of ethanol effective in the catalytic conversion of the composition to olefin product. In one embodiment of the invention, the recovered methanol composition comprises at least about 50 wt % methanol, based on total weight of the composition. Desirably, the methanol composition comprises at least about 75 wt % methanol, preferably at least about 80 wt % methanol, more preferably at least about 85 wt % methanol, and most preferably at least about 90 wt % methanol, based on total weight of the composition.

In another embodiment of the invention, the recovered methanol composition comprises not greater than 99 wt % methanol, based on total weight of the composition. Preferably, the methanol composition comprises not greater than 98 wt % methanol, more preferably not greater than 97 wt % methanol, and most preferably not greater than 96 wt % methanol, based on total weight of the composition.

In yet another embodiment of the invention, the methanol composition recovered according to the process of the invention (e.g., distilled methanol product) comprises greater than 10 wppm ethanol, based on total weight of the composition. Preferably, the methanol composition comprises at least about 100 wppm ethanol. More preferably, the methanol composition comprises at least about 1,000 wppm ethanol, still more preferably at least about 10,000 wppm ethanol, and most preferably at least about 0.1 wt % ethanol, based on total weight of the composition.

In another embodiment of the invention, the recovered or final distilled methanol composition comprises not greater than 50 wt % ethanol, based on total weight of the composition. Preferably, the recovered methanol composition comprises not greater than 40 wt % ethanol, more preferably not greater than 35 wt % ethanol, and most preferably not greater than 30 wt % ethanol, based on total weight of the recovered or final distilled composition.

In another embodiment, the recovered methanol composition includes water. The water content should not be so high that shipping costs are prohibitive, but be in sufficient quantity to exert a positive partial pressure in the methanol to olefin conversion reaction, thereby increasing selectivity to ethylene and/or propylene.

In one embodiment of the invention, the recovered methanol composition contains at least about 0.1 wt % water, based on total weight of the methanol composition. Preferably, the methanol composition contains at least about 0.15 wt % water, more preferably at least about 0.2 wt % water, and most preferably at least about 0.25 wt % water, based on total weight of the methanol composition.

In another embodiment, the recovered methanol composition contains not greater than about 2 wt % water, based on total weight of the methanol composition. Preferably, the methanol composition contains not greater than about 1.5 wt % water, more preferably not greater than about 1.2 wt % water, and most preferably not greater than about 1 wt % water, based on total weight of the methanol composition.

It is preferred that the water stream composition that is recovered from the distillation system contain only low levels of ethanol. Preferably, the ethanol level is sufficiently low such that there is not a significant load placed on any waste treatment system that is used to treat waste from the distillation system.

In one embodiment, the water stream from the distillation system comprises not greater than 10,000 wppm ethanol, based on total weight of the water stream. Preferably, the water stream from the distillation system comprises not greater than 1,000 wppm ethanol, more preferably not greater than 500 wppm ethanol, based on total weight of the water stream.

The distillation system is controlled so as to recover the preferred methanol compositions of the invention. Preferably, the distillation system is controlled so that the amount of fusel oil is reduced to a predetermined level relative to the amount of methanol recovered. In one embodiment, the methanol product stream is recovered from the distillation system at a weight ratio of the fusel oil stream recovered (i.e., fusel oil draw) to the methanol product stream recovered (i.e., methanol draw) of not greater than 0.5 to 1, preferably not greater than 0.3 to 1. Weight ratios of the fusel oil stream recovered (i.e., fusel oil draw) to the methanol product stream recovered (i.e., methanol draw) can also be as low as not greater than 0.2 to 1, 0.1 to 1 or 0.05 to 1. In certain embodiments, the ratio of the fusel oil stream recovered (i.e., fusel oil draw) to the methanol product stream recovered (i.e., methanol draw) can go down to 0, meaning that there is no fusel oil stream recovered. Thus, according to this invention, recovery of a fusel oil stream is optional.

In one embodiment of the invention a fusel oil stream or draw is recovered as a liquid stream. In a particular embodiment, the fusel oil stream is a liquid stream taken from a column fed with the crude methanol from a let-down vessel. In another embodiment, the fusel oil stream is a recovered as a bottoms liquid from a column fed with the crude methanol stream. In another embodiment, the off-take point of the fusel oil stream is at a level below the crude methanol stream feed level. Alternatively or additionally, the fusel oil stream is taken from a level above the feed level.

Examples of distillation systems include the use of single and two-column distillation columns. Preferably, the single columns operate to remove volatiles in the overhead, methanol product at a high level, optionally fusel oil as vapor above the feed and/or as liquid below the feed, and water as a bottoms draw stream.

In one embodiment of a two-column system, the first column is a "topping column" from which volatiles are taken overhead and methanol liquid as bottoms. The second is a "rectifying column" from which methanol product is taken as an overhead stream or at a high level, and water is removed as a bottoms draw stream.

In another embodiment of a two-column system, the first column is a water-extractive column in which there is a water feed introduced. Preferably, the water feed is introduced at a level above the crude methanol feed level. It is desirable to feed sufficient water to produce a bottoms liquid draw containing at least 40% w/w water, preferably at least 60% w/w water, and more preferably at least 80% w/w water. This column optionally includes one or more direct fusel oil side draws or off-takes.

In yet another embodiment, the distillation system is one in which an aqueous, semi-crude methanol is taken as liquid above the feed in a single or rectifying column. The semi-crude methanol is passed to a rectifying column, from which methanol product is taken overhead or at a high level. Preferably, water is taken as a bottoms draw stream.

III. Use of the Methanol Product Composition in the Manufacture of Olefins

The methanol product composition recovered according to this invention can be used as feed for any conventional process. Examples of such uses include the manufacture of methyl tertiary butyl alcohol (MTBE) for use in reformulated gasolines and oxygenated fuels; the use of methanol as a fuel for fuel cells, use as feedstock to make olefins, and for use in making acetic acid and formaldehyde.

The methanol product stream of this invention is particularly suited for conversion to olefins, particularly ethylene and/or propylene. The methanol product stream can be fed directly to an olefin conversion process or it can be transported in large quantities over great distances and converted to olefins.

According to this invention, the methanol product can be produced in large scale quantities for conversion to olefins, which is of great advantage for further conversion of the olefins to polyolefins such as polyethylene and polypropylene. Advantageously, this invention allows for at least 100,000 metric tons of methanol product per year. Preferably, production is at least 500,000 metric tons per year, more preferably at least 1 million metric tons per year, and most preferably at least 2 million metric tons per year.

In one embodiment, the methanol product stream of the invention is separated from a crude methanol stream, and transported to a location geographically distinct from that where the methanol composition was separated from the crude methanol stream. Preferably, the methanol composition of this invention is loaded into a vessel, and the vessel is transported over a body of water to a storage facility. The methanol can be easily transported at least 100, 500 or 1,000 miles or more. Once arriving at the storage facility, the methanol composition is delivered to a storage tank. From the storage tank, the methanol composition is ultimately sent to an olefin conversion unit for conversion to an olefin product. The methanol composition is preferably, loaded onto a ship, with the ship able to contain at least 20,000 tons, preferably at least 40,000 tons, and more preferably at least 80,000 tons.

An advantage of being able to transport the methanol product composition is that the units which produce the methanol do not have to be located in close geographic proximity to the olefin conversion unit. This makes it possible to use remote gas reserves. These remote gas reserves would be used as feed for the methanol manufacturing facility. The methanol made at these remote sites can then be easily transported to a suitable location for conversion to olefins. Since olefins and polyolefins (i.e., plastics) demands are typically low at the remote gas sites, there will generally be a desire to transport methanol to high olefins and plastic demand areas. Methanol is routinely transported in vessels that are similar to those that transport crude oil and other fuels. Examples of locations of remote gas reserves include the coastline of west Africa, northwest Australia, in the Indian Ocean, and the Arabian Peninsula. Examples of locations of preferred sites to convert methanol to other products such as olefins include the U.S. Gulf coast and northwest Europe.

IV. Converting the Methanol Product Composition to Olefins

A. General Process Description

In one embodiment of the invention, the methanol product composition obtained according to this invention is converted to olefins by contacting the methanol composition with an olefin forming catalyst to form the olefin product. The olefin product is recovered, and water, which forms during the conversion of the oxygenates in the methanol to olefins, is removed. After removing the water, the olefins are separated into individual olefin streams, and each individual olefin stream is available for further processing.

B. Description of Olefin Forming Catalyst

Any catalyst capable of converting oxygenate to olefin can be used in this invention. Molecular sieve catalysts are preferred. Examples of such catalysts include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. No. 4,822,478, 4,683,217, 4,744,885 (FeAPSO), EP-A-0 158 975 and U.S. Pat. No. 4,935,216 (ZNAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. No. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

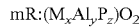

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

In one embodiment, the molecular sieves used in the invention are combined with one or more other molecular sieves. In another embodiment, the preferred silicoaluminophosphate or aluminophosphate molecular sieves, or a combination thereof, are combined with one or more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A- 0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ∈-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve, in a preferred embodiment, is combined with one or more matrix materials. Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 µm to about 0.6 µm with a D90 particle size distribution of less than about 1 µm.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

C. Adding Other Oxygenates to Methanol Composition

In an optional embodiment of this invention, the methanol composition is converted to olefin along with other oxygenates or diluents. The additional oxygenates or diluents can be co-mixed with the methanol composition or added as a separate feed stream to an oxygenate conversion reactor. In one embodiment, the additional oxygenate is one or more alcohol(s), preferably aliphatic alcohol(s) where the aliphatic moiety of the alcohol(s) has from 1 to 10 carbon atoms, preferably from 1 to 5 carbon atoms, and most preferably from 1 to 4 carbon atoms. Ethanol is most preferred. The alcohols include lower straight and branched chain aliphatic alcohols and their unsaturated counterparts. Non-limiting examples of oxygenates include ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The methanol feed stream, in one embodiment, contains one or more diluent(s), typically used to reduce the concentration of the methanol, and are generally non-reactive to the oxygenates in the composition or to the molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to the methanol feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50 more percent, most preferably from about 5 to about 25 mole percent. In one embodiment, other hydrocarbons are added to the feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

D. General Conditions for Converting Methanol to Olefins

According to the reaction process of this invention, oxygenate is contacted with olefin forming catalyst to form an olefin product, particularly ethylene and propylene. The process for converting the oxygenate feedstock is, preferably, a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

One preferred reactor type is a riser reactor. These types of reactors are generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one embodiment of the invention, a fluidized bed process or high velocity fluidized bed process includes a reactor system, catalyst separation system, and a regeneration system. The reactor system preferably is a fluid bed reactor system. In one embodiment, the fluid bed reactor system has a first reaction zone within one or more riser reactors, and a second reaction zone within at least one catalyst separation vessel, preferably comprising one or more cyclones. In one embodiment, one or more riser reactors and catalyst separation vessel is contained within a single reactor vessel.

An oxygenate stream, preferably containing one or more oxygenates, and optionally one or more diluents, is fed to a fluid bed reactor in which a molecular sieve catalyst composition is introduced. In one embodiment, the molecular sieve catalyst composition is contacted with a liquid or gas, or combination thereof, prior to being introduced to the riser reactor. Preferably, the liquid is water or methanol, and the gas is an inert gas such as nitrogen.

In one embodiment of the invention, the temperature of the regenerator is indirectly controlled by controlling the amount of heat generated in the reactor. One example of controlling the amount of heat generated is by introducing at least a portion of the oxygenate stream into the reactor in liquid form. The greater the liquid content, the less heat generated, since the exothermic heat of reaction of oxygenate conversion is partially absorbed by the endothermic heat of vaporization of the liquid portion of the feed.

In another embodiment, the amount of oxygenate stream that is fed to a reactor system in liquid form is from about 0.1 weight percent to about 85 weight percent, based on the total weight of the oxygenate stream, including any diluent contained therein. Preferably the amount of the oxygenate stream that is fed to the reactor system in liquid form is from about 1 weight percent to about 75 weight percent, more preferably from about 5 weight percent to about 65 weight percent, based on the total weight of the oxygenate stream, including any diluent contained therein.

The liquid and vapor portion of the feed may be the same composition, or may contain varying proportions of the same or different oxygenates and same or different diluents. One particularly effective liquid diluent is water, due to its relatively high heat of vaporization. Other useful diluents are described above. Proper selection of the temperature and pressure of any appropriate oxygenate and/or diluent being fed to the reactor will ensure at least a portion is in the liquid phase as it enters the reactor and/or comes into contact with the catalyst or a vapor portion of the feed and/or diluent.

Optionally, the liquid fraction of the oxygenate stream is split into portions and introduced into the reactor at a multiplicity of locations along its length. This can be done with the oxygenate feed, the diluent, or both. Preferably, this is done with the diluent portion of the feed. Another option is to provide a nozzle which introduces the total liquid fraction of the feed into the inlet zone or reactor in a manner such that the nozzle forms liquid droplets of an appropriate size distribution which, when entrained with the gas and solids introduced to the inlet zone or reactor, vaporize gradually along the length of the reactor. Either of these arrangements or a combination thereof may be used to better control the amount of heat generated. The means of introducing a multiplicity of liquid feed points in a reactor or designing a liquid feed nozzle to control droplet size distribution is well known in the art and is not discussed here.

In another embodiment of the invention, the temperature of the regenerator is controlled by circulating heat absorbing solid particles between the reactor and regenerator. The heat absorbing solid particles are substantially inert solid materials, which do not substantially adversely affect the conversion of the oxygenate to olefin. Preferably, the heat absorbing solid particles contain no molecular sieve as a part of the solid particles. However, the heat absorbing solid particles are, preferably, circulated along with the molecular sieve catalyst between the reactor and the regenerator. Suitable materials for use as heat absorbing solid particles include such materials as metals, metal oxides, and mixtures thereof. Particularly suitable materials are those used as matrices for molecular sieve catalyst formulation, e.g., fillers and binders such as silicas and aluminas, among others, and mixtures thereof. Desirably, the heat absorbing solid particles have a heat capacity of from about 0.8 cal/g-° C., and most preferably from about 0.1 to about 0.5 cal/g-° C. In another embodiment, the heat absorbing solids is present at a solids to catalyst ratio of from about 0.01–10:1, more preferably from about 0.05–5:1.

In an embodiment where catalyst and heat absorbing solid particles are circulated between the reactor and regenerator, the catalyst and heat absorbing solid particles are optionally circulated at a rate that is from about 1 to about 200 times that of the total rate of the oxygenate stream input to the reactor. Preferably, the catalyst and heat absorbing solid particles are circulated at a rate that is from about 5 to about 160 times that of the total rate of the oxygenate stream input to the reactor; more preferably from about 10 to about 100 times that of the total rate of the oxygenate stream input to the reactor.

In another embodiment, the molecular sieve catalyst itself is circulated between the reactor and regenerator at a rate of from about 1 to about 100 times that of the total rate of the oxygenate stream input to the reactor. Preferably, the molecular sieve catalyst is circulated at a rate that is from about 5 to about 80 times that of the total rate of the oxygenate stream input to the reactor; more preferably from about 10 to about 50 times that of the total rate of the oxygenate stream input to the reactor.

The oxygenate in the oxygenate feed stream entering the reactor system is preferably converted, partially or fully, in a reactor zone forming an olefin product and a coked catalyst. The olefin product and coked catalyst, as well as any unconverted or unreacted oxygenate, are sent to a catalyst separation vessel where the coked catalyst is separated from the olefin product and the unconverted or unreacted oxygenate.

In a preferred embodiment, cyclones within the separation vessel are used to separate the coked catalyst composition. Gravity effects within the disengaging vessel can also be effective in separating the catalyst. Other processss for separating the catalyst from the gaseous effluent include the use of plates, caps, elbows, and the like.

The average reaction temperature employed in the conversion process, specifically within the reactor, is of from about 250° C. to about 800° C. Preferably the average reaction temperature within the reactor is from about 250° C. to about 750 ° C.; more preferably, from about 300° C. to about 650° C.; yet more preferably from about 350° C. to about 600° C.; and most preferably from about 400° C. to about 500° C.

The pressure employed in the conversion process, specifically within the reactor, is not critical. The reaction pressure is based on the partial pressure of the feedstock exclusive of any diluent therein. Typically the reaction pressure employed in the process is in the range of from about 0.1 kPaa to about 5 MPaa, preferably from about 5 kpaa to about 1 MPaa, and most preferably from about 20 kpaa to about 500 kpaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor is preferably sufficient to fluidize the molecular sieve catalyst composition within a reaction zone of the reactor. The SGV in the process, particularly within the reactor system, more particularly within a riser reactor, is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec.

According to one embodiment, the conversion of oxygenate, particularly the conversion of methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

It is desirable to maintain an amount of coke on the catalyst in the reaction vessel to enhance the formation of desired olefin product, particularly ethylene and propylene. It is particularly desirable that the catalyst in the reactor be maintained to contain at least about 1.5 wt % coke. Preferably, the amount of coke maintained on the catalyst in the reactor should be from about 2 wt % to about 30 wt %.

V. Olefin Product Recovery and Use

In one embodiment, olefin product and other gases are withdrawn from the reactor and are passed through a recovery system. Any conventional recovery system, technique and/or sequence useful in separating olefin(s) and purifying olefin(s) from other gaseous components can be used in this invention. Examples of recovery systems include one or more or a combination of various separation, fractionation and/or distillation towers, columns, and splitters, and other associated equipment; for example, various condensers, heat exchangers, refrigeration systems or chill trains, compressors, knock-out drums or pots, pumps, and the like.

Non-limiting examples of distillation towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene ($C_2$) splitter, propylene ($C_3$) splitter, butene ($C_4$) splitter, and the like.

Various recovery systems useful for recovering predominately olefin(s), preferably prime or light olefin(s) such as ethylene, propylene and/or butene are described in U.S. Pat. No. 5,960,643, U.S. Pat. Nos. 5,019,143, 5,452,581 and 5,082,481, U.S. Pat. No. 5,672,197, U.S. Pat. No. 6,069,288, U.S. Pat. No. 5,904,880, U.S. Pat. No. 5,927,063, and U.S. Pat. No. 6,121,504, U.S. Pat. No. 6,121,503, and U.S. Pat. No. 6,293,998, which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428, U.S. Pat. No. 6,293,999, and U.S. patent application Ser. No. 09/689,363 filed Oct. 20, 2000, which are herein incorporated by reference.

The ethylene and propylene streams produced and recovered according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4+$ olefins, particularly butylene, separated according to this invention. The olefins separated according to this invention can also be used in the manufacture of such compounds as aldehydes, acids such as $C_2$–$C_{13}$ mono carboxylic acids, alcohols such as $C_2$–$C_{12}$ mono alcohols, esters made from the $C_2$–$C_{12}$ mono carboxylic acids and the $C_2$–$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4+$ olefins, butylene in particular, are particularly suited for the manufacture of aldehydes, acids, alcohols, esters made from $C_5$–$C_{13}$ mono carboxylic acids and $C_5$–$C_{13}$ mono alcohols and linear alpha olefins.

VI. EXAMPLES OF THE INVENTION

Example 1

SAPO-34 molecular sieve catalyst was used to evaluate the conversion of certain alcohols to olefins. Experiments were performed with the use of a microflow reactor. Typically, 95 mg of formulated catalyst or 38 mg of sieve was mixed with 1 g of 100-μm silicon carbide. The mixture was loaded into the reactor, which is made of ¼" silicon steel tubing. The reactor temperature was increased to 475° C. while the catalyst was under He flow (46 ml/min), and waited for ca. 30 to 40 min for the temperature to stabilize. Methanol was used as the feedstock, and was flowed through reactor at ca. 80 μl/min at 475C, 25 psig and 100 WHSV. The reactor effluent was sampled in a multi-loop sampling valve to obtain the gas phase selectivity data. The collected effluent samples were analyzed by on-line gas chromatography (Hewlett Packard 6890) equipped with a flame ionization detector. The chromatographic column used was a Q-column.

The weighed average yields were calculated based on the following formula:

$$x_1*y_1+(x_2-x_1)*y_2+(x_3-x_2)*(y_2+y_3)/2+(x_4-x_3)*(y_3+y_4)/2+\ldots,$$

where $x_i$ and $y_i$ are yield and g methanol fed/g sieve, respectively. Note that WHSV was reported based on the weight of the sieve. Methanol converted at less than ca. 10% conversions was not counted in the calculations. Selectivities were calculated by normalizing the yield data excluding methanol, DME, methyl ethyl ether, ethyl ether and the added component, e.g., ethanol and acetaldehyde. The result is shown in Table 1.

Example 2

The procedure of Example 1 was repeated, except that a mixture of 2.5 wt % ethanol and 97.5 wt % methanol was used as the feedstock. The result is shown in Table 1.

TABLE 1

| Feed | $C_1$ (wt %) | $C_2$= (wt %) | $C_2$o (wt %) | $C_3$= (wt %) | $C_3$o (wt %) | $C_4$ (wt %) | $C_5$+ (wt %) | $C_{2+3}$= (wt %) |
|---|---|---|---|---|---|---|---|---|
| 100 wt % methanol | 1.83 | 36.53 | 0.29 | 40.72 | 0.57 | 13.71 | 6.36 | 77.25 |
| 2.5 wt % ethanol + 97.5 wt % methanol | 1.47 | 38.38 | 0.26 | 39.79 | 0.48 | 13.71 | 5.91 | 78.17 |

In Table 1, the terms $C_1$, $C_2$=, $C_2$o, $C_3$=, $C_3$o, $C_4$, $C_5$+, and $C_{2+3}$= refer, respectively, to methane, ethylene, ethane, propylene, propane, butenes and butanes, hydrocarbons that contain five or more than five carbons, and ethylene and propylene. The values shown in Table 1 indicate that ethylene and propylene yield is improved, as well as selectivity to ethylene, with a methanol feed that contains ethanol.

Example 3

A simulation of a methanol refining column was run using SimSci's ProII simulation model. The simulation included a topping column to remove light components (e.g., hydrogen, carbon dioxide, methane, dimethyl ether) and a refining column to recover methanol product. The refining column was modeled as a distillation column having 76 stages, a reflux ratio of 3.1, condenser temperature of 166° F., and reboiler temperature of 327° F. The crude methanol feed composition to the column was set as shown in Table 2:

TABLE 2

| Feed Component | Amount (lb/hr) |
|---|---|
| Methanol | 117636 |
| Ethanol | 41541 |
| Isopropanol | 113 |
| Water | 52374 |
| $H_2$ | 14 |
| $CH_4$ | 84 |
| $CO_2$ | 99 |
| dimethyl ether | 104 |

The column was set to have an overhead draw and a bottoms draw, with no side draw. The bottoms draw was set to have an ethanol concentration limit of 100 wppm.

The simulation was run to determine water and ethanol content of the distilled methanol product from the refining column overhead draw and the composition of the water stream from the bottoms draw. The results are shown in Table 3.

TABLE 3

| Component | Overhead Draw (lb/hr) | Bottoms Draw (lb/hr) |
|---|---|---|
| Methanol | 117413 | 0 |
| Ethanol | 41533 | 5 |
| Isopropanol | 113 | 0 |
| Water | 1607 | 50767 |
| $H_2$ | 0 | 0 |
| $CH_4$ | 0 | 0 |
| $CO_2$ | 0 | 0 |
| Dimethyl ether | 0 | 0 |

Table 3 demonstrates that crude methanol containing ethanol and water can be distilled to recover a substantial portion of the ethanol in the feed, without having to recover a substantial quantity of water in the over head, and with recovering little to no side draw. Thus, substantially all of the methanol and ethanol in the methanol crude can be recovered as a distilled product, and the bottoms draw can be readily handled as a waste stream, since it contains relatively little hydrocarbon material.

Having now fully described this invention, it will be appreciated by those skilled in the art that the invention can be performed within a wide range of parameters within what is claimed, without departing from the spirit and scope of the invention.

We claim:

1. A process for making a methanol product stream, the process comprising the steps of:
   a) contacting a synthesis gas with a carbon oxide conversion catalyst to form a crude methanol stream;
   b) distilling the crude methanol stream in a distillation system to form a methanol product stream, a water containing stream, and, a fusel oil containing stream; and
   c) recovering the methanol product stream from the distillation system at a weight ratio of the fusel oil containing stream to the methanol product stream of not greater than 0.5 to 1, wherein the methanol product stream contains at least 100 wppm ethanol.

2. The process of claim 1, wherein the methanol product stream is recovered at a weight ratio of the fusel oil stream to the methanol product stream of not greater than 0.3 to 1.

3. The process of claim 2, wherein the methanol product stream is recovered at a weight ratio of the fusel oil stream to the methanol product stream of not greater than 0.2 to 1.

4. The process of claim 3, wherein the methanol product stream is recovered at a weight ratio of the fusel oil stream to the methanol product stream of not greater than 0.1 to 1.

5. The process of claim 4, wherein the methanol product stream is recovered at a weight ratio of the fusel oil stream to the methanol product stream of not greater than 0.05 to 1.

6. The process of claim 5, wherein the methanol product stream is recovered at a weight ratio of the fusel oil stream to the methanol product stream of down to 0.

7. The process of claim 1, wherein the methanol product stream contains at least 0.1 wt % water.

8. The process of claim 7, wherein the methanol product stream contains not greater than 2 wt % water.

9. The process of claim 1, wherein the methanol product stream contains not greater than 99 wt % methanol.

10. The process of claim 1, wherein the methanol product stream contains not greater than 50 wt % ethanol.

11. The process of claim 1, wherein the water containing stream contains not greater than 10,000 wppm ethanol.

12. The process of claim 11, wherein the water containing stream contains not greater than 1,000 wppm ethanol.

13. The process of claim 12, wherein the water containing stream contains not greater than 500 wppm ethanol.

14. The process of claim 1, wherein the recovered methanol product stream is transported to a location geographically distinct from that where it was recovered.

15. The process of claim 1, wherein the recovered methanol product stream is contacted with an olefin forming catalyst to form an olefin stream.

16. The process of claim 15, wherein the olefin stream is contacted with a polymerization catalyst to form a polyolefin.

17. A process for making a methanol product stream, the process comprising the steps of:
   a) contacting a synthesis gas with a carbon oxide conversion catalyst to form a crude methanol stream;
   b) distilling the crude methanol stream in a distillation system; and
   c) recovering from the distillation system a methanol product stream as an overhead stream containing at least 0.1 wt % and not greater than 2 wt % water and at least 100 wppm ethanol, a water containing stream as a bottoms stream containing not greater than 10,000 wppm ethanol, and a fusel oil stream as a side draw stream.

18. The process of claim 17, wherein the methanol product stream is recovered at a weight ratio of the fusel oil stream to the methanol product stream of not greater than 0.5 to 1.

19. The process of claim 18, wherein the methanol product stream is recovered at a weight ratio of the fusel oil stream to the methanol product stream of not greater than 0.3 to 1.

20. The process of claim 19, wherein the methanol product stream is recovered at a weight ratio of the fusel oil stream to the methanol product stream of not greater than 0.2 to 1.

21. The process of claim 20, wherein the methanol product stream is recovered at a weight ratio of the fusel oil stream to the methanol product stream of not greater than 0.05 to 1.

22. The process of claim 21, wherein the methanol product stream is recovered at a weight ratio of the fusel oil stream to the methanol product stream of down to 0.

23. The process of claim 17, wherein the methanol product stream contains at least 0.1 wt % water.

24. The process of claim 17, wherein the methanol product stream contains not greater than 2 wt % water.

25. The process of claim 17, wherein the methanol product stream contains not greater than 99 wt % methanol.

26. The process of claim 17, wherein the methanol product stream contains not greater than 50 wt % ethanol.

27. The process of claim 26, wherein the water containing stream contains not greater than 10,000 wppm ethanol.

28. The process of claim 27, wherein the water containing stream contains not greater than 1,000 wppm ethanol.

29. The process of claim 28, wherein the water containing stream contains not greater than 500 wppm ethanol.

30. The process of claim 17, wherein the recovered methanol product stream is transported to a location geographically distinct front that where it was recovered.

31. The process of claim 17, wherein the recovered methanol product stream is contacted with an olefin forming catalyst to form an olefin stream.

32. The process of claim 31, wherein the olefin stream is contacted with a polymerization catalyst to form a polyolefin.

33. A process for making an olefin stream, the process comprising the steps of:
   a) contacting a synthesis gas with a carbon oxide conversion catalyst to form a crude methanol stream;
   b) distilling the crude methanol stream to form a methanol product stream, a water containing stream, and a fusel oil containing stream, at a weight ratio of the fusel oil containing stream to the methanol containing stream of not greater than 0.5 to 1, wherein the methanol product stream contains at least 100 wppm ethanol; and
   c) contacting the methanol product stream with an olefin forming catalyst to form an olefin stream.

34. The process of claim 33, wherein the methanol product stream is recovered at a weight ratio of the fusel oil stream to the methanol product stream of not greater than 0.3 to 1.

35. The process of claim 34, wherein the methanol product stream is recovered at a weight ratio of the fusel oil stream to the methanol product stream of not greater than 0.2 to 1.

36. The process of claim 35, wherein the methanol product stream is recovered at a weight ratio of the fusel oil stream to the methanol product stream of not greater than 0.1 to 1.

37. The process of claim 36, wherein the methanol product stream is recovered at a weight ratio of the fusel oil stream to the methanol product stream of not greater than 0.05 to 1.

38. The process of claim 37, wherein the methanol product stream is recovered at a weight ratio of the fusel oil stream to the methanol product stream of down to 0.

39. The process of claim 33, wherein the methanol product stream contains at least 0.1 wt % water.

40. The process of claim 33, wherein the methanol product stream contains not greater than 2 wt % water.

41. The process of claim 40, wherein the methanol product stream contains not greater than 99 wt % methanol.

42. The process of claim 33, wherein the methanol product stream contains not greater than 50 wt % ethanol.

43. The process of claim 42, wherein the water containing stream contains not greater than 10,000 wppm ethanol.

44. The process of claim 43, wherein the water containing stream contains not greater than 1,000 wppm ethanol.

45. The process of claim 44, wherein the water containing stream contains not greater than 500 wppm ethanol.

46. The process of claim 41, wherein the recovered methanol product stream is transported to a location geographically distinct from that where it was recovered.

47. The process of claim 46, wherein the olefin stream is contacted with a polymerization catalyst to form a polyolefin.

48. A process for making polyolefin, the process comprising the steps of:
   a) contacting a synthesis gas with a carbon oxide conversion catalyst to form a crude methanol stream;
   b) distilling the crude methanol stream in a distillation system to form a methanol product stream, a water containing stream and a fusel oil stream at a weight ratio of the fusel oil stream to the methanol product stream of not greater than 0.5 to 1, wherein the methanol product stream contains at least 100 wppm ethanol;
   c) contacting the methanol product stream with an olefin forming catalyst to form an olefin stream; and
   d) contacting the olefin stream with a polymerization catalyst to form a polyolefin.

49. The process of claim 48, wherein the methanol product stream is recovered at a weight ratio of the fusel oil stream to the methanol product stream of not greater than 0.3 to 1.

50. The process of claim 48, wherein the methanol product stream is recovered at a weight ratio of the fusel oil stream to the methanol product stream of not greater than 0.2 to 1.

51. The process of claim 48, wherein the methanol product stream is recovered at a weight ratio of the fusel oil stream to the methanol product stream of not greater than 0.1 to 1.

52. The process of claim 48, wherein the methanol product stream is recovered at a weight ratio of the fusel oil stream to the methanol product stream of not greater than 0.05 to 1.

53. The process of claim 48, wherein the methanol product stream is recovered at a weight ratio of the fusel oil stream to the methanol product stream of down to 0.

54. The process of claim 48, wherein the methanol product stream contains at least 0.1 wt % water.

55. The process of claim 48, wherein the methanol product stream contains not greater than 2 wt % water.

56. The process of claim 48, wherein the methanol product stream contains not greater than 99 wt % methanol.

57. The process of claim 48, wherein the methanol product stream contains not greater than 50 wt % ethanol.

58. The process of claim 48, wherein the water containing stream contains not greater than 1,000 wppm ethanol.

59. The process of claim 48, wherein the water containing stream contains not greater than 1,000 wppm ethanol.

60. The process of claim 48, wherein the water containing stream contains not greater than 500 wppm ethanol.

61. The process of claim 48, wherein the recovered methanol product stream is transported to a location geographically distinct from that where it was recovered.

62. The process of claim 1, 17, 33 or 48, wherein the methanol product stream comprises at least 1,000 wppm ethanol.

63. The process of claim 62, wherein the methanol product stream comprises at least 10,000 wppm ethanol.

64. The process of claim 63, wherein the methanol product stream comprises at least 0.1 wt % ethanol.

* * * * *